United States Patent [19]

Haugwitz et al.

[11] E Re. 30,990

[45] Reissued Jul. 6, 1982

[54] BENZIMIDAZOLE DERIVATIVES, COMPOSITIONS THEREOF AND METHOD OF USE AS ANTHELMINTICS

[75] Inventors: Rudiger D. Haugwitz; Barbara V. Maurer, both of Titusville, N.J.

[73] Assignee: E. R. Squibb & Sons, Inc., Princeton, N.J.

[21] Appl. No.: 186,823

[22] Filed: Sep. 12, 1980

Related U.S. Patent Documents

Reissue of:

[64] Patent No.: 4,046,908
Issued: Sep. 6, 1977
Appl. No.: 706,040
Filed: Jul. 16, 1976

[51] Int. Cl.[3] ..... A61K 31/415; C07D 235/32

[52] U.S. Cl. ..... 424/273 B; 424/263; 424/273 R; 548/306; 546/271

[58] Field of Search ..... 546/271; 548/306; 424/263, 273 B

[56] References Cited

U.S. PATENT DOCUMENTS 3,929,821 12/1975 Beard et al. ..... 260/309.2
3,929,823 12/1975 Beard et al. ..... 260/309.2
4,138,493 2/1979 Haugwitz et al. ..... 548/306
4,258,198 3/1981 Gyurik et al. ..... 548/306

OTHER PUBLICATIONS

Burger, "Medicinal Chemistry", (Interscience), (1951), vol. 1, pp. 31, 32, 34 and 35.

*Primary Examiner*—Robert T. Bond
*Attorney, Agent, or Firm*—Lawrence S. Levinson; Burton Rodney

[57] ABSTRACT

Benzimidazolederivatives are provided having the structure wherein $R^1$ is lower alkyl, phenyl-lower alkyl, halo-lower alkyl, mono-lower alkylaminoalkyl, di-lower alkylaminoalkyl, and alkyl pyridinium halide, $R^2$ and $R^3$ may be the same or different and are hydrogen or lower alkyl, $R^4$ is cycloalkyl or cycloalkenyl, and m is 0 to 3, n is 0 to 3, m+n being $\leqq 5$. These compounds are useful as anthelmintic agents.

3 Claims, No Drawings

BENZIMIDAZOLE DERIVATIVES, COMPOSITIONS THEREOF AND METHOD OF USE AS ANTHELMINTICS

Matter enclosed in heavy brackets [ ] appears in the original patent but forms no part of this reissue specification; matter printed in italics indicates the additions made by reissue.

The present invention relates to benzimidazole derivatives having the structure

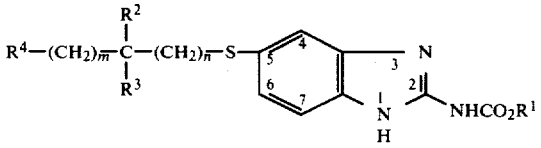

I wherein $R^1$ is lower alkyl, phenyl-lower alkyl, halo-lower alkyl, mono-lower alkylaminoalkyl, di-lower alkylaminoalkyl, and alkyl pyridinium halide $R^2$ and $R^3$ may be the same or different and are hydrogen or lower alkyl, and $R^4$ is cycloalkyl or cycloalkenyl, m is 0 to 3, n is 0 to 3 and m+n is $\leqq 5$.

The term "halogen" or "halo" as used throughout the specification refers to fluorine, chlorine, bromine, and iodine; chlorine is preferred.

The term "lower alkyl" as used herein includes straight or branched chain aliphatic hydrocarbon radicals having up to and including seven carbon atoms, such as methyl, ethyl, propyl, isopropyl, butyl, isobutyl, t-butyl, amyl, hexyl, heptyl and the like.

$(CH_2)_m$ and $(CH_2)_n$ represent a single bond or straight or branched chain alkylene radicals containing 3 or less carbons in the longest normal chain.

The term "alkyl pyridinium halide" refers to a radical of the structure

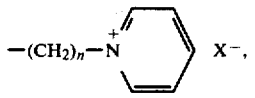

wherein $(CH_2)_n$, represents a straight or branched chain alkyl radical containing from 2 to 5 carbons in the longest normal chain and X is Cl or Br.

The term "phenyl lower alkyl" as used herein refers to lower alkyl groups as discussed above having a phenyl substituent, such as benzyl.

The term "cycloalkyl" includes cyclic hydrocarbon groups containing 3 to 12 carbons, while the term "cycloalkenyl" includes cyclic hydrocarbon groups containing 3 to 10 carbons. Examples of suitable cycloalkyl and cycloalkenyl groups include cyclopropyl, cyclobutyl, cyclopentyl, cyclohexyl, cycloheptyl, cyclooctyl, cyclodecyl and cyclododecyl, cyclopropenyl, cyclobutenyl, cyclohexenyl, cycloheptenyl, cyclononeyl and cyclodecenyl, any of which groups may be substituted with 1, 2, 3 or 4 halogen or lower alkyl groups. In the above cycloalkenyl rings, the double bond may be at any position in the ring.

Preferred are those compounds wherein $R^1$ is methyl, ethyl, propyl or benzyl, or dimethylaminopropyl, m is 0, n is 0, $R^2$ is hydrogen, $R^3$ is hydrogen or methyl, $R^4$ is cyclopropyl, cyclohexyl, cyclooctyl, 2,2-dichlorocyclopropyl or cyclohexen-3-yl.

Examples of preferred compounds falling within the present invention include the following.

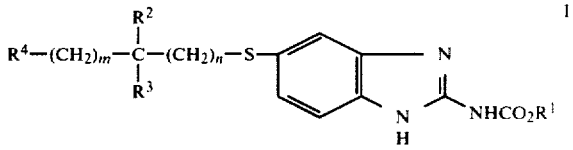

I

| | $R^1$ | $R^2$ | $R^3$ | $R^4$ | $(CH_2)_m$ | $(CH_2)_n$ |
|---|---|---|---|---|---|---|
| 1. | $CH_3$ | H | H | 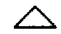 | — | — |
| 2. | $CH_3$ | H | H | 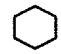 | — | — |
| 3. | $CH_3$ | H | H | 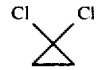 | — | — |
| 4. | $C_2H_5$ | $CH_3$ | H | 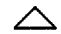 | — | — |
| 5. | $CH_3$ | H | H | 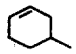 | — | — |
| 6. | $C_6H_5CH_2$ | H | H | 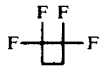 | — | — |
| 7. | $C_3H_7$ | H | H | 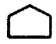 | — | — |
| 8. | $CH_3$ | H | H | 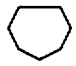 | — | — |
| 9. | $C_6H_5CH_2$ | H | H | 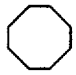 | — | — |
| 10. | $C_3H_7$ | H | H | 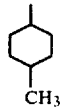 | — | — |
| 11. | $(CH_3)_2NC_2H_4$ | H | $C_2H_5$ | 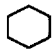 | $CH_2$ | — |
| 12. | $C_2H_5NHC_3H_6$ | H | H | 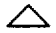 | — | $CH_2$ |
| 13. | $ClC_3H_6$ | $CH_3$ | $CH_3$ | 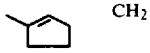 | $CH_2$ | $CH_2$ |
| 14. | 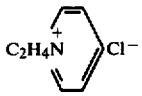 | H | H | 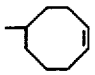 | — | — |

The benzimidazole derivatives of structure I may be prepared by thiocyanation of o-nitroaniline to yield 4-thiocyano-2-nitroaniline (II). This product is then subjected to a sodium borohydride reduction to yield the corresponding 4-mercapto-2-nitroaniline (III). The mercapto derivative may be isolated or used directly for the next step. Thus, to the reaction mixture there is added the haloalkyl cycloalkane or haloalkyl cycloalkene IV to furnish the sulfide V.

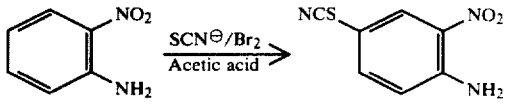

II

-continued
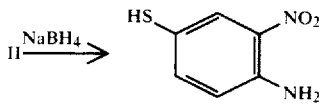
III
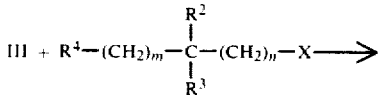
(wherein X is Cl or Br)
IV
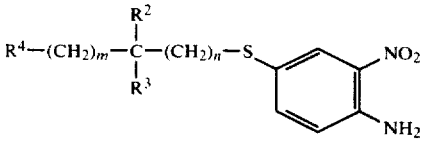
V
Examples of suitable haloalkyl cycloalkanes and haloalkyl cycloalkenes of formula IV suitable for use herein include the following:
Cyclopropane
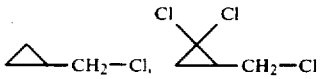
Cyclopropene
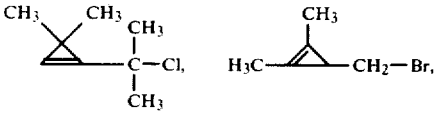
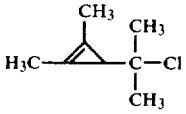
Cyclobutane
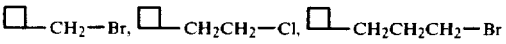
Cyclobutene
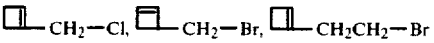
Cyclopentane
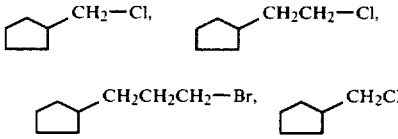
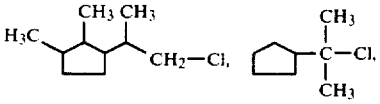
-continued
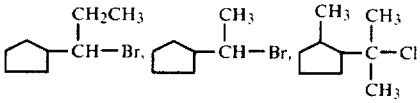
Cyclopentene
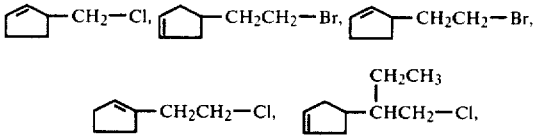
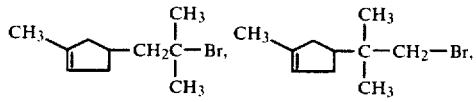
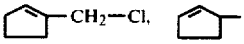
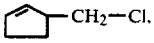
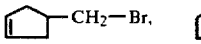
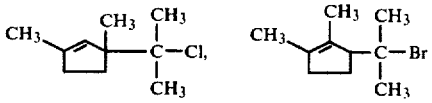
Cyclohexane
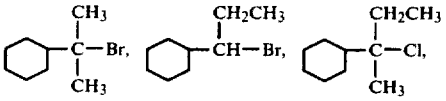
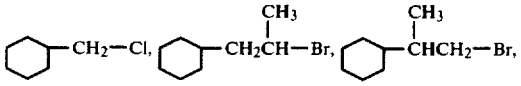
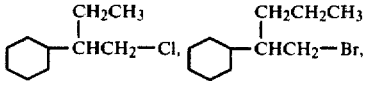
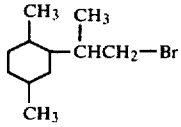
Cyclohexene
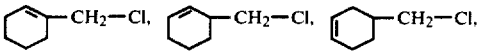
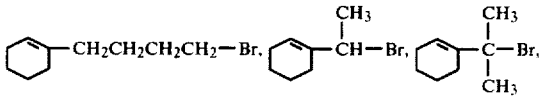
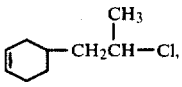
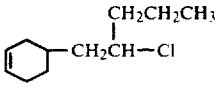
Cycloheptane -continued

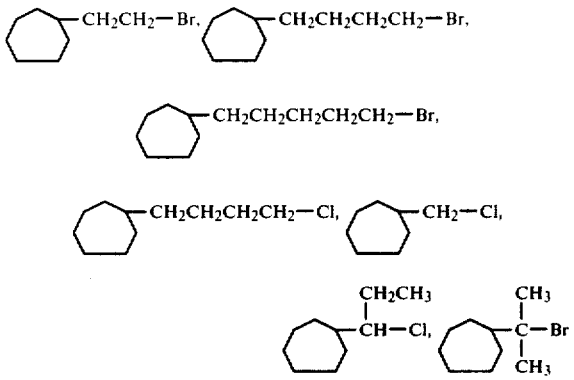

Cycloheptene

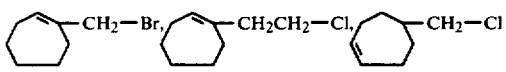

Cyclooctane

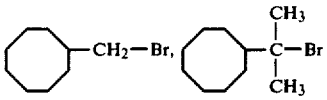

Cyclooctene

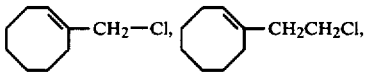

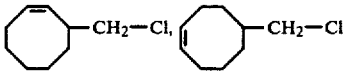

Cyclononane

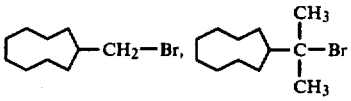

Cyclononene

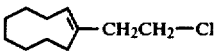

Cyclodecane

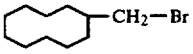

Cyclodecene

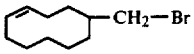

Cycloundecane

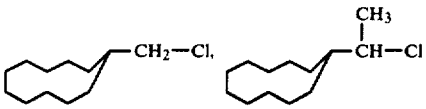

Cyclododecene

-continued

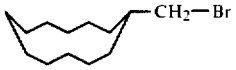

The resulting sulfides may be purified by crystallization and then reduced to the corresponding o-phenylene diamine VI. Either chemical or catalytic reduction may be used. For the chemical reduction the procedure outlined by Sandler and Caro (Organic Functional Group Preparations, 1968, pp 339–340) is preferred. The final step in the synthesis of I, namely ring closure of VI to furnish I, can be achieved in various ways. Whereas refluxing of VI with the isolated thiourea derivative VII in alcohols such as methanol or ethanol will furnish I, the preferred method of preparing I is by forming VII in situ and then without isolating it adding VI and refluxing it for 30 minutes to 5 hours to yield the desired product.

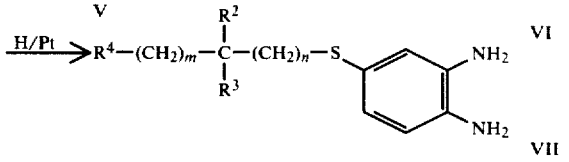

or

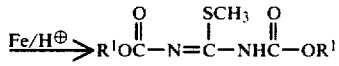

An alternative route toward the intermediate VI offers the reaction of VIII with the requisite mercaptoalkyl cycloalkane or cycloalkene IX, to yield X. Here, in contrast to the alkylation step described above, (i.e., IV→V) the reaction temperature has to be higher and the reaction periods have to be longer. Reduction of X yields the desired diamine VI

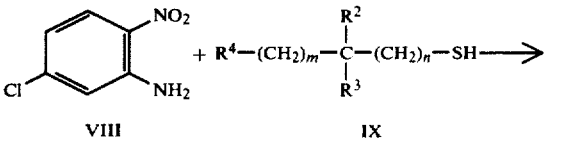

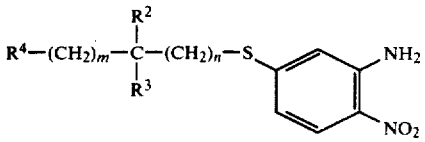

A great variety of haloalkyl cycloalkanes IV are commercially available. In some cases the requisite haloalkyl cycloalkane has to be synthesized. For example, the addition of dichlorocarbene to allyl bromide furnishes the cyclopropyl derivative IV

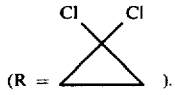

Additions of other than dichlorocarbene are possible, such as, monochlorocarbene, dibromocarbene, and the like.

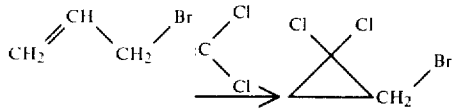

The requisite haloalkyl cycloalkanes or cycloalkenes may also be prepared from the corresponding alcohols by standard reactions.

In certain instances, the compounds of formula I form physiologically acceptable acid-addition salts with inorganic and organic acids, for example, where $R^1$ contains an amino function as indicated above. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

The compounds of formula I have anthelmintic activity and are useful in the treatment and/or prevention of helminthiasis, a parasitic disease which causes widespread and often serious infection in domesticated animals such as swine, horses, cattle, dogs, cats and sheep. The compounds are useful in treating infections caused by Haemonchus, Ostertagia, Trichostrongylus, Cooperia, dictyocaulus, Nematodirus, Bunostomum, Strongyloides, Oesophagostomum, Trichiuris and Moniezia. In treating domesticated animals, the compounds are given orally; however, other routes such as subcutaneously may be employed. Where the compounds are administered orally, they may be mixed with a nontoxic, edible carrier to form a feed supplement, or be administered in unit dosage forms such as powders, capsule, tablet, boluses, drenches, etc.

In general, the compound of formula I exhibit anthelmintic activity when administered to animals in a single dose of from about 5 to about 100 mg per kilogram of animal body weight. It is preferred to employ in the range of 5–25 mg per kilogram of body weight. The compounds may be given in a single dose or divided into a plurality of smaller doses.

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1–2%. Lastly, feeds containing the active ingredient may be made directly by mixing said active ingredients in a feed which is inert to said anthelmintic compounds so as to give feeds having concentrations of anthelmintic agent of from 0.1–2%.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

2-Nitro-4-thiocyanoaniline

To a well-stirred mixture of 108 g of o-nitroaniline and 128 g of ammonium thiocyanate in 400 ml of acetic acid there is added dropwise a solution of 128 g of bromine in 160 ml of acetic acid below 20° C. The mixture is stirred for 4 hours at room temperature and then poured into 4 liters of water. The resulting solid is filtered off and crystallized from ethanol to yield 86.7 g, m.p. 111°–114° C.

EXAMPLE 2

4-(Cyclohexylmethyl)thio-2-nitroaniline

To a stirred mixture of 9.75 g (0.05 mole) of 2-nitro-4-thiocyanoaniline in 500 ml of absolute ethanol under nitrogen there is added 2.04 g (0.05 mole) of sodium borohydride in portions. The mixture is stirred at room temperature for 15 minutes and then refluxed for 15 minutes.

The heating mantle is removed and 3.25 g (0.05 mole) of KOH in 15 ml of absolute ethanol is added. The mixture is stirred for 1 minute. A solution of 8.85 g (0.05 mole) of cyclohexylmethyl bromide in 15 ml of absolute ethanol is added and the mixture is stirred at room temperature for 15 minutes then refluxed for 1 hour. Equal amounts of water and $CHCl_3$ are added until 2 layers are formed. The organic layer is separated, dried ($MgSO_4$) and the solvent removed in vacuo. The residue is crystallized from ethyl ether to yield 8.3 g, m.p. 80°–82°.

EXAMPLE 3

4-(Cyclohexylmethyl)thio-o-phenylenediamine

A mixture of 8.0 g (0.03 mole) of 4-(cyclohexylmethyl)thio-2-nitroaniline and 0.5 g of $PtO_2$ in 200 ml of absolute ethanol is reduced on the Parr hydrogenator at 50 psi until the theoretical amount of $H_2$ is absorbed. The mixture is filtered and the solvent is removed in vacuo to yield the solid diamine, m.p. 76°–79° C.

EXAMPLE 4

[5-[(Cyclohexylmethyl)thio]-1H-benzimidazol-2-yl]carbamic acid, methyl ester To a mixture of 9 g of 2-methyl-2-thiopseudourea sulfate in 6 ml of water there is added 5.7 ml of methyl chloroformate at 0° C. and the mixture is stirred for 15 minutes. Then there is added 12 ml of 25% NaOH dropwise and the mixture is stirred for 15 minutes. Then the total amount of 4-(cyclohexylmethyl)thio-o-phenylenediamine from the above reaction in 50 ml of methanol is added and the mixture is refluxed for 2 hours. The alcohol is removed in vacuo and water is added. The resulting solid is filtered off and crystallized from $CH_3CN$ to yield 2.5 g, m.p. 200°-204° C.

EXAMPLE 5

4-(Cyclopropylmethyl)thio-2-nitroaniline

To a stirred mixture of 11.7 g (0.06 mole) of 2-nitro-4-thiocyanoaniline in 500 ml of absolute ethanol under nitrogen there is added 2.5 g (0.06 mole) of sodium borohydride in portions. The mixture is stirred at room temperature for 15 minutes and then refluxed for 15 minutes. The heating mantle is removed and 3.9 g (0.06 mole) of KOH in 25 ml of absolute ethanol is added. The mixture is stirred for 1 minute. A solution of 4.8 g (0.06 mole) of (chloromethyl) cyclopropane in 10 ml of absolute ethanol is added and the mixture is stirred at room temperature for 15 minutes then refluxed for 2 hours. Equal amounts of water and $CHCl_3$ are added until 2 layers are formed. The organic layer is separated, dried ($MgSO_4$), and the solvent removed in vacuo to give 9.1 g of an orange-red solid, m.p. 45°-47°.

EXAMPLE 6

4-(Cyclopropylmethyl)thio-o-phenylenediamine

A mixture of 6.75 g (0.03 mole) of 4-(cyclopropylmethyl)thio-2-nitroaniline and 0.5 g of $PtO_2$ in 200 ml of absolute ethanol is reduced on the Parr hydrogenator at 50 psi. The mixture is filtered and the solvent is removed in vacuo to yield the solid diamine, m.p. 57°-60° C.

EXAMPLE 7

[5-[(Cyclopropylmethyl)thio)-1H-benzimidazol-2-yl]carbamic acid, methyl ester To a mixture of 9 g of 2-methyl-2-thiopseudourea sulfate in 6 ml of water there is added 5.7 ml of methyl chloroformate at 0° C. and the mixture is stirred for 15 minutes. Then there is added 12 ml of 25% NaOH dropwise and the mixture is stirred for 15 minutes. Then there is added 6 ml of acetic acid dropwise and the mixture is stirred for 15 minutes. The total amount of 4-(cyclopropylmethyl)thio-o-phenylenediamine from above in 50 ml of methanol is then added and the mixture is refluxed for 2 hours. The alcohol is removed in vacuo and water is added. The resulting solid is filtrated off and crystallized from glyme-acetonitrile to yield, 3.9 g, m.p. 228°-231°.

EXAMPLE 8

[5-[(Cyclopropylmethyl)thio]-1H-benzimidazol-2-yl]carbamic acid, benzyl ester Following the procedure of Example 4 and substituting benzyl chloroformate for methyl chloroformate, the title comound is obtained.

EXAMPLE 9

[5-[(2,2,3,3-Tetrafluorocyclobutylmethyl)thio]-1H-benzimidazol-2-yl]carbamic acid, methyl ester Following the procedures of Examples 5-7 and substituting 1-chloromethyl-2,2,3,3-tetrafluorocyclobutane for cyclohexylmethyl bromide the title compound is obtained.

EXAMPLE 10

[5-[(2,2-Dichlorocyclopropylmethyl)thio]-1H-benzimidazol-2-yl]carbamic acid, methyl ester A. 4-[(2,2-dichlorocyclopropyl)methyl]thio-2-nitroaniline To a stirred mixture of 11.75 g (0.06 mole) of 2-nitro-4-thiocyanoaniline in 500 ml of absolute ethanol under $N_2$ there is added 2.5 g (0.06 mole) of sodium borohydride in portions. The mixture is stirred at room temperature for 15 minutes and then refluxed for 15 minutes. The heating mantle is removed and 3.9 g (0.06 mole) of KOH in 30 ml of absolute ethanol is added. The mixture is stirred for 1 minute. A solution of 12.25 g (0.06 mole) of 1-bromomethyl-2,2-dichlorocyclopropane in 30 ml of absolute ethanol is added and the mixture is stirred at room temperature for 15 minutes and then refluxed for 2 hours. Equal amounts of $H_2O$ and $CHCl_3$ are added until 2 layers are formed. The organic layer is separated, dried ($MgSO_4$), and the solvent removed in vacuo to give a red oil which is chromatographed on silica gel. Elution with ethyl ether gives 9.6 g of red oil.

B. 4-[(2,2-Dichlorocyclopropyl)methyl]thio-o-phenylenediamine

A mixture of 8.8 g (0.03 mole) of 4-[(2,2-dichlorocyclopropyl)methyl]thio-2-nitroaniline and 0.6 g of $PtO_2$ in 200 ml of absolute ethanol is reduced on the Parr hydrogenator at 50 psi until the theoretical amount of $H_2$ is absorbed. The mixture is filtered and the solvent is removed in vacuo to yield a dark oil.

C. [5-[(2,2-Dichlorocyclopropylmethyl)]thio]-1H-benzimidazol-2-yl]carbamic acid, methyl ester To a mixture of 9 g of 2-methyl-2-thiopseudourea sulfate in 6 ml of $H_2O$ there is added 5.7 ml of methyl chloroformate at 0° C. and the mixture is stirred for 15 minutes. Then there is added 12 ml of 25% NaOH dropwise and the mixture is stirred for 15 minutes. Then there is added 6 ml of acetic acid dropwise and the mixture is stirred for 15 minutes. Then the total amount of 4-[(2,2-dichlorocyclopropyl)methyl]thio-o-phenylenediamine from above in 50 ml of methanol is added and the mixture is refluxed for 2 hours. The alcohol is removed in vacuo and $H_2O$ is added. The resulting solid is filtered off and cyystallized from glyme to yield 5.4 g, m.p. 211°-213°.

EXAMPLE 11

[5-[(Cyclohexen-3-ylmethyl)thio]-1H-benzimidazol-2-yl]-carbamic acid, 3-dimethylaminopropyl ester A mixture of 0.01 mole of the methyl ester of Example 4 and 0.02 mole of 3-dimethylamino-1-propanol is refluxed in 20 ml of toluene until all the $H_2O$ present has been azeotroped off. The heating mantle is removed and 0.25 g of aluminum isopropoxide is added. The mixture is then refluxed overnight. After cooling the solid present is filtered off, washed with water and crystallized.

EXAMPLES 12 to 25

Following the procedure of Examples 1 to 4 except substituting for cyclohexylmethyl bromide the compound shown in column I of Table I below and substituting for methyl chloroformate the compound shown in column II, the product shown in column III is obtained.

TABLE I

| | Column I | | | Column II | Column III | |
|---|---|---|---|---|---|---|
| | $R^4-(CH_2)_m-\underset{R^3}{\overset{R^2}{C}}-(CH_2)_n-X$ | | | $HCOOR^1$ | $R^4-(CH_2)_m-\underset{R^3}{\overset{R^2}{C}}-(CH_2)_n-S$ 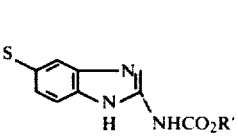 | |
| Ex. No. | $R^4$ | $-(CH_2)_m-\underset{R^3}{\overset{R^2}{C}}-(CH_2)_n-$ | X | $R^1$ | $R^4-(CH_2)_m-\underset{R^3}{\overset{R^2}{C}}-(CH_2)_n$ | $R^1$ |
| 12. | 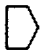 | $-\overset{CH_2CH_3}{\overset{\vert}{CH}}-$ | Cl | $n\text{-}C_3H_7$ | as in Column I | as in Column II |
| 13. | 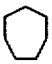 | $-\overset{C_2H_5}{\overset{\vert}{CH}}-$ | Br | $C_2H_4Cl$ | | |
| 14. | 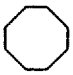 | $-\overset{CH_3}{\underset{CH_3}{C}}-$ | Cl | $(CH_2)_4NHCH_3$ | | |
| 15. | 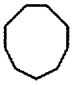 | $-(CH_2)_2-$ | Br | $(CH_2)_3N(C_2H_5)_2$ | | |
| 16. | 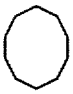 | $-CH_2-$ | Cl | 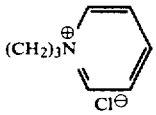 | | |
| 17. | 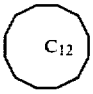 | $-CH_2-$ | Br | $C_2H_5$ | | |
| 18. | 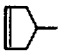 | $-\overset{C_2H_5}{\overset{\vert}{CH}}CH_2-$ | Cl | $CH_2\overset{CH_3}{\overset{\vert}{C}}HCl$ | | |
| 19. | 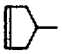 | $-CH_2-$ | Br | $(CH_2)_2\overset{CH_3}{\overset{\vert}{C}}HNHC_2H_5$ | | |
| 20. | 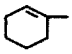 | $-(CH_2)_2$ | Cl | $N(CH_3)_2$ | | |
| 21. | 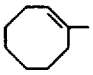 | $-(CH_2)_2-$ | Br | 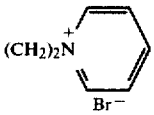 | | |
| 22. | 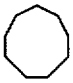 | $-(CH_2)_2$ | Cl | $n\text{-}C_4H_9$ | | |
| 23. | 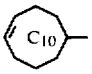 | $-CH_2-$ | Br | $C_2H_4C_6H_5$ | | |
| 24. | 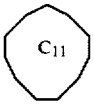 | $-\overset{CH_3}{\overset{\vert}{CH}}-$ | Cl | $CH_3$ | | |
| 25. | 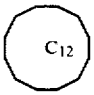 | $-CH_2-$ | Br | $CH_3$ | | |

What is claimed is:

[1. A compound of the structure

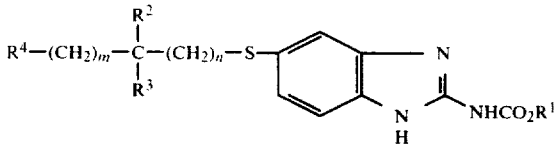

wherein $R^1$ is lower alkyl, phenyl-lower alkyl, halo-lower alkyl, mono lower alkylaminoalkyl, and alkyl pyridinium halide, $R^2$ and $R^3$ are the same or different and are selected from the group consisting of hydrogen or lower alkyl, and $R^4$ is cycloalkyl containing 3 to 12 carbons or cycloalkenyl containing 3 to 10 carbons, m is 0 to 3, n is 0 to 3 and m+n is $\leqq 5$, and physiologically acceptable salts thereof where $R^1$ includes an amino function.]

[2. The compound as defined in claim 1 wherein $R^1$ is lower alkyl or benzyl.]

[3. The compound as defined in claim 1 wherein $R^2$ and $R^3$ are hydrogen or methyl.]

[4. The compound as defined in claim 1 wherein m is 0 and n is 0, and $R^2$ and $R^3$ are hydrogen.]

[5. The compound as defined in claim 1 having the name [5-[(cyclopropylmethyl)thio]-1H-benzimidazol-2-yl]-carbamic acid, methyl ester.]

[6. The compound as defined in claim 1 having the name [5-[(cyclohexylmethyl)thio]-1H-benzimidazol-2-yl]-carbamic acid, methyl ester.]

7. [The] *A* compound [as defined in claim 1] having the name [5-[(2,2-dichlorocyclopropylmethyl)thio]-1H-benzimidazol-2-yl]carbamic acid, methyl ester.

[8. The compound as defined in claim 1 having the name [5-[(cyclohexen-3-yl methyl)thio]-1H-benzimidazol-2-yl]-carbamic acid, 3-dimethyl-aminopropyl ester.]

9. A pharmaceutical composition for use in treating helminthiasis comprising a therapeutically effective amount of a compound as defined in claim [1] *7* and a pharmaceutically acceptable carrier therefor.

10. A method for treating helminthiasis which comprises administering to a mammalian host a therapeutically effective amount of the composition as defined in claim 9.

* * * * *

UNITED STATES PATENT AND TRADEMARK OFFICE

CERTIFICATE OF CORRECTION

PATENT NO. : RE. 30,990

DATED : July 6, 1982

INVENTOR(S) : Rudiger D. Haugwitz et al.

It is certified that error appears in the above—identified patent and that said Letters Patent is hereby corrected as shown below:

On the title page, first line of the Abstract, "Benzimidazolederivatives" should read --Benzimidazole derivatives--.

Column 8, line 7, "ingredients" should read --ingredient--.

Column 11, Table I, Ex. 19, Column I, under the heading "$R^4$" the structure should read " 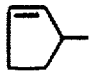 ".

Signed and Sealed this

Eighth Day of February 1983

[SEAL]

Attest:

GERALD J. MOSSINGHOFF

Attesting Officer

Commissioner of Patents and Trademarks